US00PP24845P3

(12) United States Plant Patent
Danziger

(10) Patent No.: US PP24,845 P3
(45) Date of Patent: Sep. 2, 2014

(54) ***PETUNIA* PLANT NAMED 'DMARV121'**

(50) Latin Name: *Petunia sensu wijsman*
Varietal Denomination: DMARV121

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 56 days.

(21) Appl. No.: 13/694,739

(22) Filed: Dec. 27, 2012

(65) Prior Publication Data

US 2014/0189921 P1 Jul. 3, 2014

(51) Int. Cl.
*A01H 5/00* (2006.01)

(52) U.S. Cl.
USPC ..... Plt./356.13

(58) Field of Classification Search
USPC ..... Plt./356.13
See application file for complete search history.

*Primary Examiner* — Kent L Bell
(74) *Attorney, Agent, or Firm* — Cassandra Bright

(57) ABSTRACT

A new and distinct *Petunia* cultivar named 'DMARV121' is disclosed, characterized by medium sized flowers that are Pink-red with Red-purple veins and a Yellow center. The new variety also has a compact, ball-shaped, well branched growth habit. The new variety is an *Petunia*, normally produced as an outdoor garden or container plant.

2 Drawing Sheets

Figure 1:
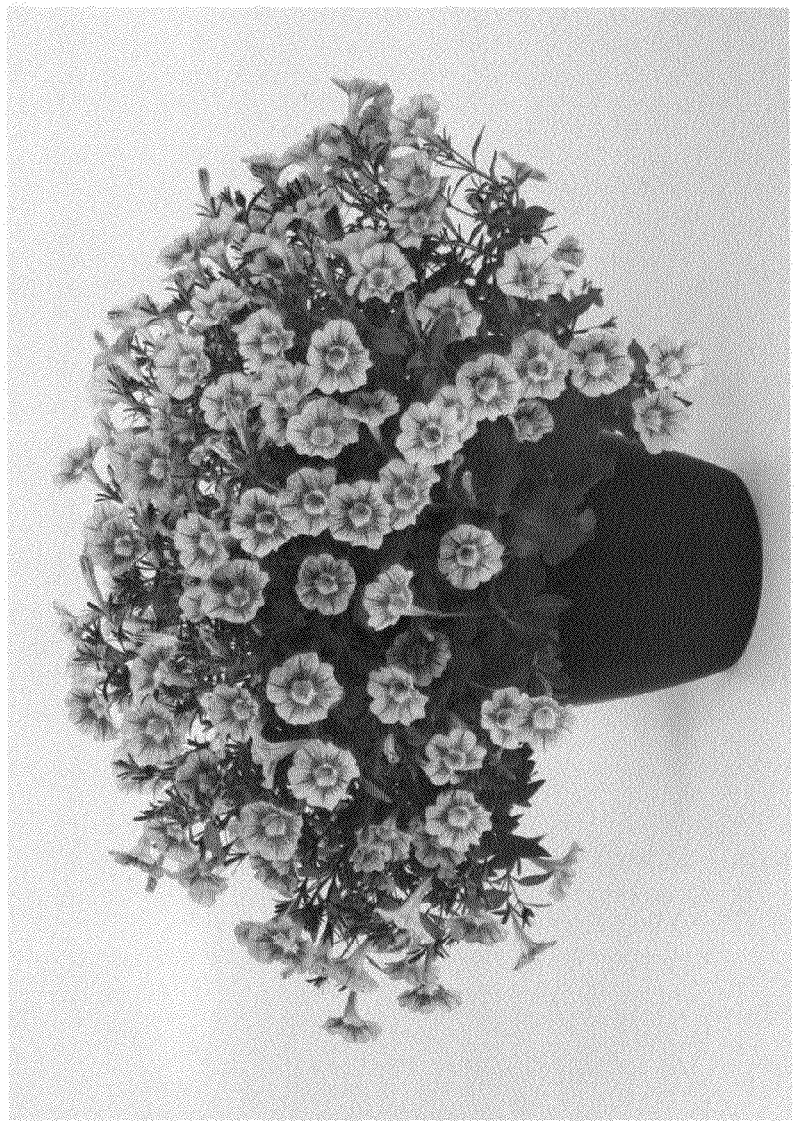

Latin name of the genus and species: *Petunia sensu wijsman.*

Variety denomination: 'DMARV121'.

BACKGROUND OF THE INVENTION

The new *Petunia* cultivar is a product of a planned breeding program conducted by the inventor, Gavriel Danziger, in Moshav Mishmar Hashiva, Israel. The objective of the breeding program was to produce new *Petunia* varieties for ornamental commercial applications. The cross resulting in this new variety was made during February of 2010.

The seed parent is the unpatented proprietary variety referred to as *Petunia sensu wijsman.* '10-3675'. The pollen parent is the unpatented proprietary variety referred to as *Petunia sensu wijsman* '10-3529'. The new variety was discovered in November of 2010 by the inventor in a group of seedlings resulting from the February 2010 crossing, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in December of 2010 and has shown that the unique features of this cultivar are stable and reproduced true to type over several successive generations.

SUMMARY OF THE INVENTION

The cultivar 'DMARV121' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DMARV121' These characteristics in combination distinguish 'DMARV121' as a new and distinct *Petunia* cultivar:

1. Mounded, ball-shaped plant.
2. Compact and very well branched plant.
3. Flowers are Pink-red, with Red-purple veins and a Yellow center.
4. Flower size is medium.
5. Abundant flowering.

PARENT COMPARISON

Plants of the new cultivar 'DMARV121' are similar to plants of the seed parent, *Petunia sensu wijsman* '10-3675' in most horticultural characteristics, however, plants of the new cultivar 'DMARV 121' flowers more abundantly, producing smaller flowers of a different coloration. 'DMARV121' also produces a mounded ball-shaped plant whereas the seed parent produces a semi upright plant. Finally 'DMARV121' produces a more compact and more branched growth plant form than the seed parent.

Plants of the new cultivar 'DMARV121' are similar to plants of the pollen parent; *Petunia sensu wijsman* '10-3529' in most horticultural characteristics, however, plants of the new cultivar 'DMARV121' produce a mounded, ball-shaped form and a very well branched plant whereas the pollen parent produces a trailing form and is not nearly as well branched. 'DMARV121' also produces more abundant flowering and a flower of different coloration than the pollen parent. cl COMMERCIAL COMPARISON Plants of the new cultivar 'DMARV121' are comparable to the variety *Petunia* 'Dancaspispark' unpatented. The two *Petunia* varieties are similar in most horticultural characteristics; however, the new variety 'DMARV121' differs in having smaller leaf and flower size, as well as a different flower coloration. Also 'DMARV121' produces a plant that is ball-shaped and very well branched whereas 'Dancaspispark' produces a semi-upright, less well branched plant.

Plants of the new cultivar 'DMARV121' can also be compared to the commercial variety *Petunia* 'DANLITTUN1', U.S. Plant Pat. No. 19,458. These varieties are similar in most horticultural characteristics; however 'DMARV121' produces larger flowers of different coloration, as well as larger leaf size. Plants of 'DMARV121' are also less compact, ball shaped and have more branches than plants of 'DANLITTUN1', which are semi-upright and more compact.

BRIEF DESCRIPTION OF THE PHOTOGRAPHS

The accompanying photograph in FIG. 1 illustrates in full color a typical plant of 'DMARV121' grown in a greenhouse, in a 13 cm pot. Age of the plant photographed is approximately 3 months from a rooted cutting.

Figure 2:
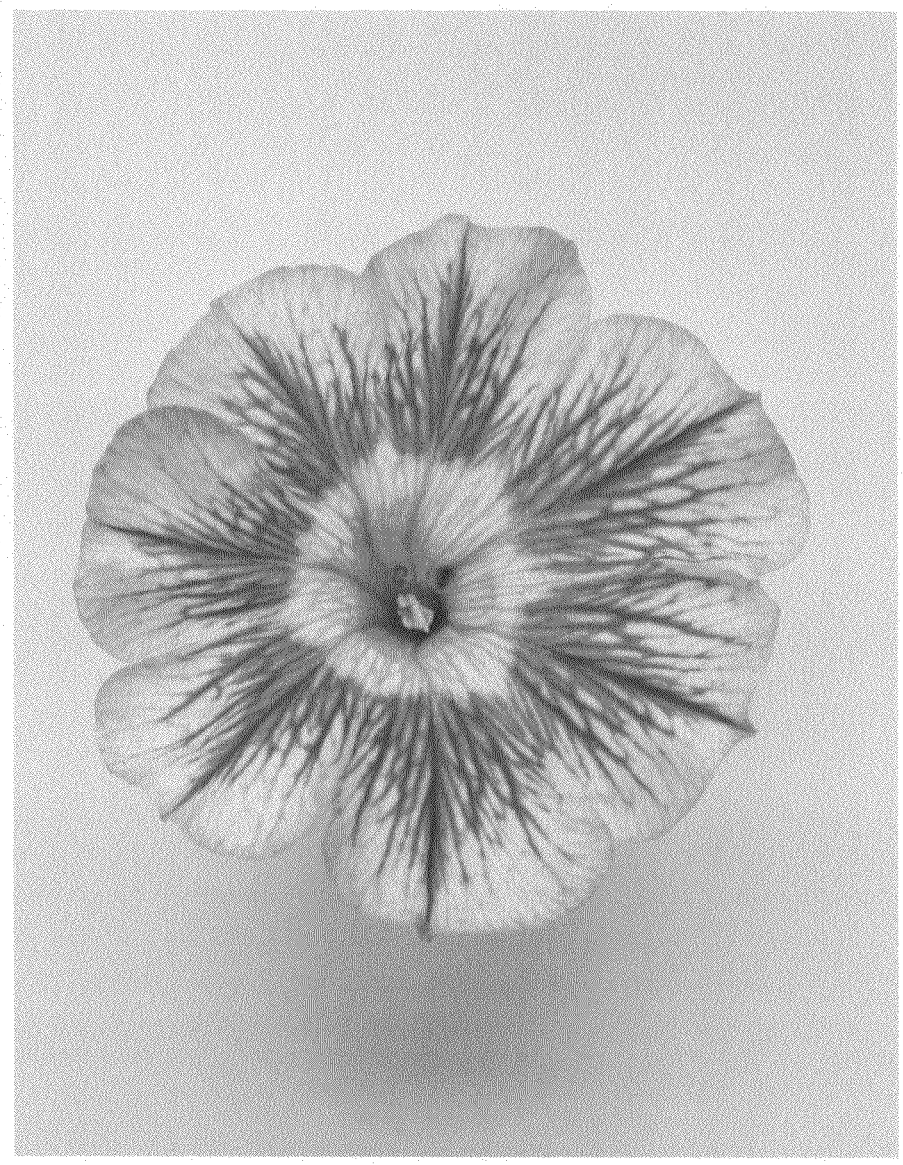

FIG. 2 illustrates in full color a close up of a typical bloom of 'DMARV121'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DMARV121' plants grown in a greenhouse, in Moshav Mishmar Hashiva, Israel. The growing temperature ranged from 20° C. to 35° C. during the day and from 17° C. to 23° C. during the night. General light conditions are bright, normal sunlight. Measurements and numerical values represent averages of typical plant types.

Botanical classification: *Petunia sensu wijsman* 'DMARV121'.

PROPAGATION

Time to initiate roots: About 10 to 14 days at approximately 22° C.

Root description: Fibrous.

PLANT

Age of plant described: Approximately 60 days from a rooted cutting.

Growth habit: Mounded

Pot size of plant described: 13 cm.

Height: 20 cm.

Plant spread: 50 cm.

Growth rate: Medium.

Branching characteristics: Very branched.

Length of primary lateral branches: About 20 cm.

Quantity of primary lateral branches: 8.

Characteristics of primary lateral branches:

- *Form*.—Cylindrical.
- *Diameter*.—About 0.4 cm.
- *Color*.—RHS Yellow-Green 144 A.
- *Texture*.—Pubescent.
- *Strength*.—Good.

Internode length: About 1 cm.

FOLIAGE

Leaf:

- *Arrangement*.—Opposite.
- *Quantity*.—Approximately 16 per branch.
- *Average length*.—4.5 cm.
- *Average width*.—2 cm.
- *Shape of blade*.—Elliptic.
- *Apex*.—Acute.
- *Base*.—Acute.
- *Margin*.—Entire.
- *Texture of top surface*.—Velvety.
- *Pubescence*.—Pubescent.
- *Aspect*.—90 degrees.
- *Color*.—Young foliage upper side: RHS Green 137 B. Young foliage under side: RHS Green 137 C. Mature foliage upper side: RHS Green 137 B. Mature foliage under side: RHS Green 137 C.
- *Venation*.—Type: Pinnate. Venation color upper side: RHS Green 137 C. Venation color under side: RHS Green 137 C.
- *Petiole*.—Length: About 0.5 cm. Diameter: About 0.1 cm. Color: RHS Green 137 B.
- *Texture*.—Velvety.

FLOWER

Natural flowering season: Spring, Summer and Autumn.

Days to flowering from rooted cutting: About 30 days.

Inflorescence and flower type and habit: Axillary, single flower, Salverform shape, Erect habit.

Rate of flower opening: 2 to 3 days from bud to fully opened flower.

Flower longevity on plant: 3-6 days.

Approximate quantity of flowers per plant: About 70.

Persistent or self-cleaning: Self-cleaning.

Bud:

- *Shape*.—Tubular.
- *Length*.—About 3.5 cm.
- *Diameter*.—About 0.7 cm.
- *Color*.—RHS Yellow-Green 145 A.

Flower size:

- *Diameter*.—About 4 cm.
- *Flower tube length*.—About 3 cm.
- *Flower tube diameter at distal end*.—1 cm.
- *Flower tube diameter at proximal end*.—0.3 cm.

Petals:

- *Length from throat*.—About 1.5 cm.
- *Width*.—About 2 cm.
- *Quantity*.—5.
- *Texture*.—Velvety.
- *Apex*.—Blunt.
- *Margin*.—Entire.

Color:

- *When opening*.—Upper surface: RHS Red-Purple 63 C, with dark veins: Red-Purple 60 A and a Yellow Center: RHS Yellow 13 A. Lower surface: RHS Red 56 C.
- *Fully opened*.—Upper surface: RHS Red-Purple 65 A, with dark veins: RHS Red-Purple 58 A and a Yellow Center: RHS Yellow 12 A. Lower surface: RHS Red 56 C. Flower throat (inside): RHS Yellow 12 A. Flower throat, vein: RHS Green 143 C. Flower tube (outside): RHS Green-Yellow 1 B. Flower tube, vein: RHS Green 143 C.
- *Fading*.—Petals fading to: RHS Red-Purple 65 C, with dark veins: Red-Purple 60 D and a Yellow Center: RHS Yellow 12 C.

Calyx/sepals:

- *Quantity per flower*.—5.
- *Shape*.—Linear.
- *Length*.—About 1.5 cm.
- *Width*.—About 0.4 cm.

*Apex*.—Rounded.
*Base*.—Cuneate.
*Margin*.—Entire.
*Texture*.—Velvety. Color: Upper Surface: RHS Green 137 B. Lower Surface: RHS Green 137 C.

Peduncle:
*Length*.—About 3 cm.
*Diameter*.—About 0.2 cm.
*Color*.—RHS Green 137 B.
*Orientation*.—45 degrees.

Fragrance: None.

REPRODUCTIVE ORGANS

Stamens:
*Number*.—5.
*Filament length*.—About 1.8 cm.

Anthers:
*Length*.—About 0.1 cm.
*Shape*.—Rounded.
*Color*.—RHS Yellow 2 D.
*Pollen*.—
*Color*.—RHS Yellow 2 D. Quantity: Plenty.

Pistil:
*Number*.—1.
*Length*.—About 2.4 cm.
*Style*.—Length: About 2 cm. Color: RHS Yellow-Green 154 D.
*Stigma*.—Shape: Rounded. Color: RHS Yellow-Green 145 C. Ovary Color: RHS Green 143 B.

OTHER CHARACTERISTICS

Seeds and fruits: About 30 brown, rounded seeds of about 0.5 mm diameter, per one brown, conical capsule.
Disease/pest resistance: Common to cultivar.
Temperature tolerance: 5-40° C.

What is claimed is:

1. A new and distinct cultivar of *Petunia* plant named 'DMARV121' as herein illustrated and described.

* * * * *